United States Patent
Brown

(10) Patent No.: US 6,307,876 B1
(45) Date of Patent: Oct. 23, 2001

(54) LINEAR ACCELERATOR

(75) Inventor: Kevin John Brown, Horsham (GB)

(73) Assignee: Elekta AB, Stockholm (SE)

(*) Notice: Subject to any disclaimer, the term of this patent is extended or adjusted under 35 U.S.C. 154(b) by 0 days.

(21) Appl. No.: 09/582,009

(22) PCT Filed: Dec. 10, 1998

(86) PCT No.: PCT/GB98/03684

§ 371 Date: Jun. 20, 2000

§ 102(e) Date: Jun. 20, 2000

(87) PCT Pub. No.: WO99/34866

PCT Pub. Date: Jul. 15, 1999

(30) Foreign Application Priority Data

Jan. 8, 1998 (GB) .................................................. 9800256

(51) Int. Cl.⁷ .................................................. A61N 5/10
(52) U.S. Cl. .................................................. 375/65
(58) Field of Search .................................................. 378/65

(56) References Cited

U.S. PATENT DOCUMENTS

| | | |
|---|---|---|
| 4,172,979 | 10/1979 | Morrison . |
| 4,230,129 | 10/1980 | Leveen . |
| 5,386,453 | 1/1995 | Harrawood et al. . |
| 5,615,430 | 4/1997 | Nambu et al. . |
| 5,894,503 | * 4/1999 | Shepherd et al. .................... 378/65 |

FOREIGN PATENT DOCUMENTS

| | | |
|---|---|---|
| 10 26 040 | 3/1958 | (DE) . |
| 15 16 402 | 1/1970 | (DE) . |
| 0 562 585 A2 | 3/1993 | (EP) . |
| WO 94 13205 | 6/1994 | (WO) . |
| WO 97 13552 | 4/1997 | (WO) . |
| WO 97 35641 | 10/1997 | (WO) . |

* cited by examiner

Primary Examiner—Craig E. Church

(57) ABSTRACT

Apparatus for treatment by radiotherapy, comprises a patient table, a directional radiation source directed generally toward the patient table, the table and source being movable relative to each other at least axially with respect to the table and rotationally around the axis, the source being directionally adjustable within at least a plane including the longitudinal axis of the table, and including means to correlate axial relative motion of the table and directional adjustment of the source. Thus, the source of such an apparatus can be rotated about the table to access the predetermined position along a series of cones centered on the predetermined position and of the variable angle. Thus, the apparatus effectively accesses the predetermined position via lines of latitude rather than longitude. It is preferred if the source is directionally adjustable across an included angle of at least 20°, preferably more than 30°. The source can be (for example) held within a ring member centered substantially on the patient table.

5 Claims, 2 Drawing Sheets

LINEAR ACCELERATOR

Figure 1:
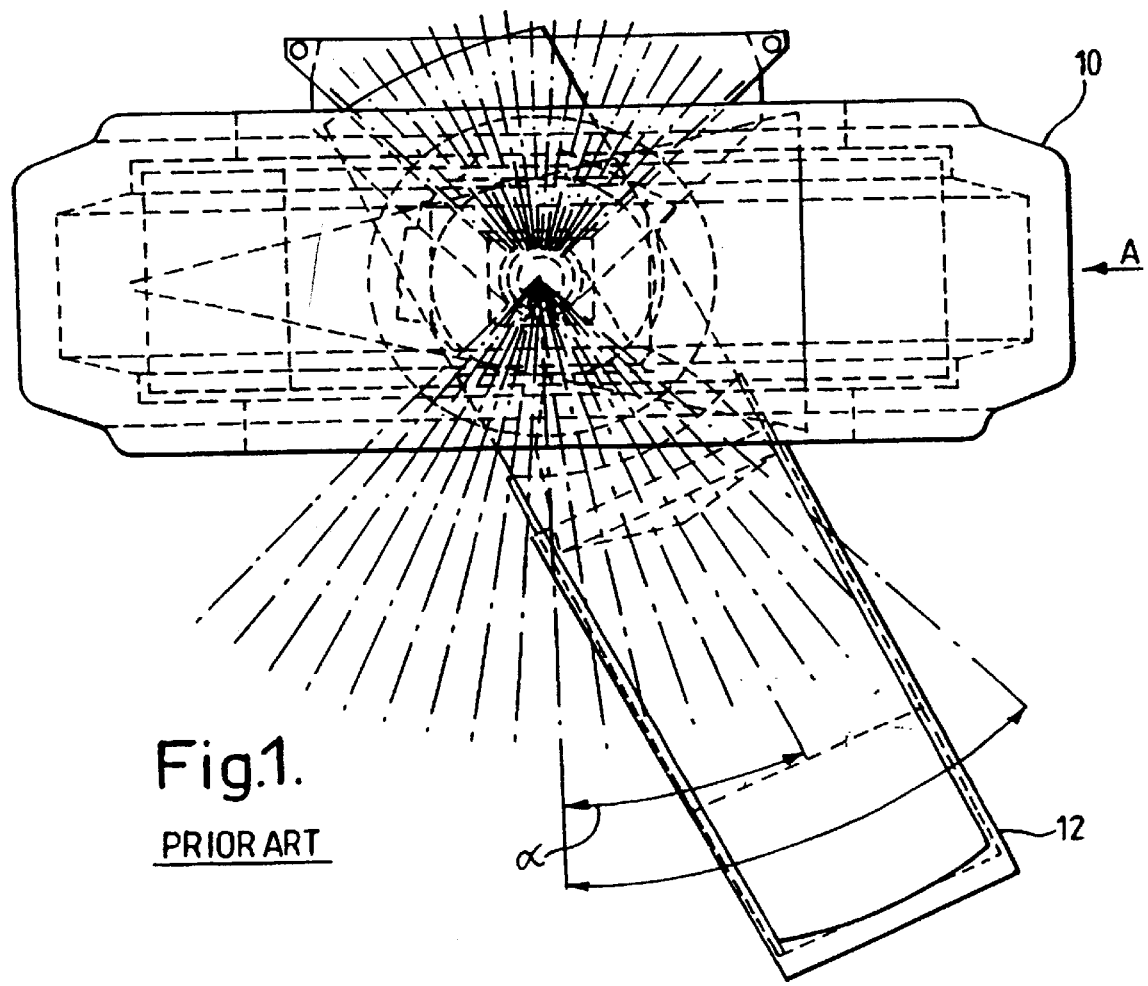

The present invention relates to a linear accelerator for therapeutic use.

The overall geometry of a linear accelerator is ideally constructed so as to enable the output beam of the radiation source to be directed at any chosen site within the patient. In order to avoid excessive doses being applied to healthy tissue, the incident direction is normally varied throughout the treatment period, the various directions each converging on a single point. This single point thereby receives a full dose whilst the surrounding areas receive only a minimal dose.

For this reason, the radiation source is normally rotatable about the longitudinal axis of the table. In our application WO 97/13552, we described a system in which the table was rotatable about its vertical axis. This provided a system in which access to a designated area within the patient could also be obtained via a plurality of directions lying along lines of longitude. This permitted a combination of rotations of the source and of the table, further reducing the dose applied to surrounding areas. However, in this arrangement, the range of directions is limited by the maximum relative rotation of the table. This rotation must be limited in order to prevent the table obstructing the rotational path of the radiation source.

Another system available from the applicant involves a plurality of small Cobalt sources arranged in the sphere and directed toward the centre of that sphere. Each source can be concealed or revealed via a suitable shutter, allowing control over dosage aspect. However, it is impractical to provide further collimation of individual beam sources due to the sheer number of individual sources present. Also, the system is in practice limited to use for treating the head as the Cobalt sources need to be near the patient in order to be effective. It is also impractical to add an imaging structure.

The present invention therefore provides an apparatus for treatment by radiotherapy, comprising:
a patient table
a directional radiation source directed generally toward the patient table,
the table and source being movable relative to each other at least axially with respect to the table and rotationally around that axis,
the source being directionally adjustable within at least a plane including the longitudinal axis of the table;
and including means to correlate axial relative motion of the table and directional adjustment of the source.

Thus, the source of such an apparatus can be rotated about the table to access the predetermined position along a series of cones centred on the predetermined position and of the variable angle. Thus, the apparatus effectively accesses the predetermined position via lines of latitude rather than longitude. This largely eliminates the inaccessible zone provided by the system of WO 97/13552, and avoids a single convergence point directly above and below the predetermined point. it also provides a single radiation source which can therefore be collimated to provide accurate beam shaping and intensity control.

Thus, whilst existing arrangements maintain an isocentre fixed relative to the source just above the patient table, the present invention does not, instead compensating by movement of the patient table.

It is preferred if the source is directionally adjustable across an included angle of at least 20°, preferably more than 30°.

The source is suitably held within a ring member centred substantially on the patient table.

Figure 2:
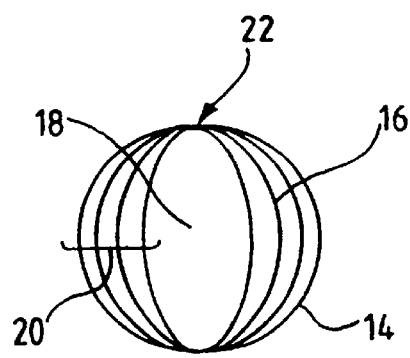
Figure 3:
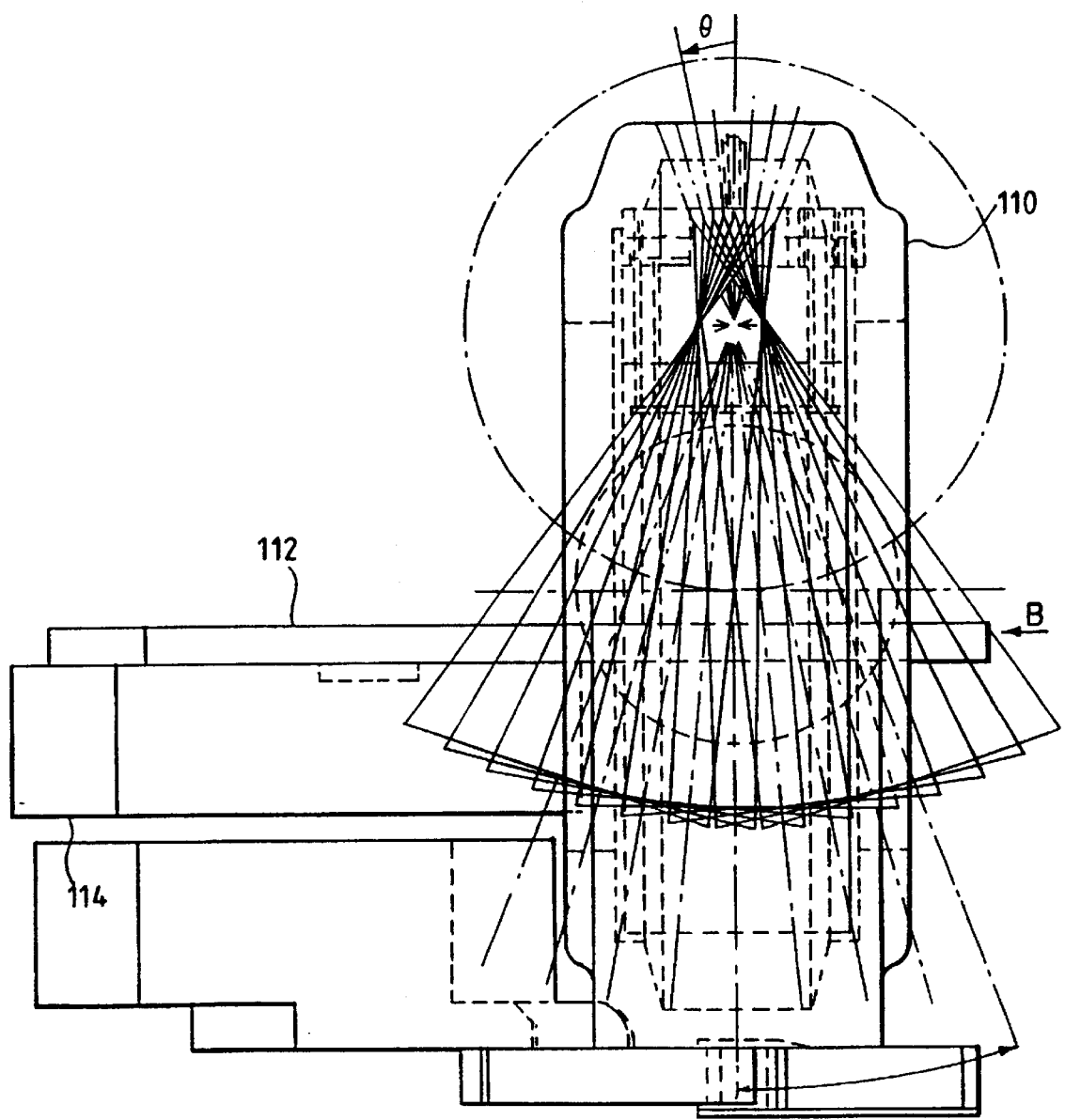
Figure 4:
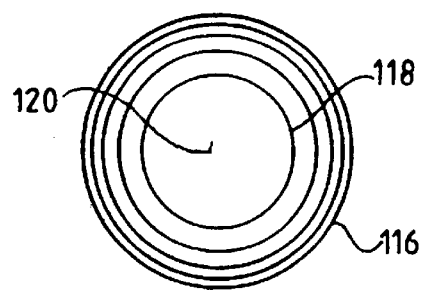

An embodiment of the present invention will now be described by way of example, with reference to the accompanying Figures, in which:

FIG. 1 is a plan view of a known linear accelerator;
FIG. 2 is an illustration of the available irradiation directions of the apparatus of FIG. 1 in the direction of arrow A of FIG. 1;
FIG. 3 is a side view of a linear accelerator according to the present invention; and
FIG. 4 is an illustration of the available irradiation directions of the apparatus of FIG. 3, in the direction of arrow B of FIG. 3.

Referring to FIG. 1, illustrating a known arrangement, a ring shaped member 10 includes within its annulus a linear accelerator directed towards the centre of the ring. The linear accelerator can be rotated within the ring so as to take up any position and thereby direct a beam of radiation toward the centre of the ring from any direction. A patient table 12 is placed so as to pass through the ring at an angle α, positioned slightly below the centre of the ring 10 such that a patient placed on the table will intersect that centre.

During treatment, the linear accelerator is rotated continuously about the ring 10, such that the directional approach of the radiation beam passes through all directions in the plane defined by the ring 10. This serves to concentrate the radiation dose at the centre of the ring and minimise it in the surrounding tissue.

The angle α can be varied, effecting rotation of the patient table about a vertical axis passing through the centre of the ring 10. This is done during treatment, so that, relative to the patient, the plane of the radiation beam direction rotates. This further minimises the dose applied to surrounding tissue without affecting the dose applied to the focal point of the beam.

The physical arrangement of the apparatus does however impose a limitation on the maximum and minimum values of α. Put simply, rotation of the table beyond these limits will cause it to foul the ring 10. Furthermore, the plane of the radiation beam direction always passes through the line which passes vertically through the focal point, meaning that the tissue immediately above and below the tumour receives a higher dose, although much reduced when compared with the tumour. This is illustrated in FIG. 2, in which a sphere 14 is irradiated, representing for example an idealised human head. Lines 16 show the path taken by the radiation beam, assuming that the angle α is increased incrementally by discrete intervals. In a genuine treatment session, α would of course be varied as smoothly as possible.

It will be seen that there is a gap 18 which is not irradiated. This means that the "unwanted" irradiation must be concentrated into the area 20. Furthermore, there is a point 22 above and below the focal point at which the lines 16 all intersect and at which precaution must be taken to avoid applying a higher dose.

Whilst in practice these limitations do not hinder the medical effectiveness of the system, it is always preferable to reduce the dosage to healthy tissue. This can be achieved via the apparatus illustrated in FIG. 3.

In FIG. 3, a ring 110 contains a linear accelerator which can be both rotated around the ring and tilted by an angle θ away from the vertical. A patient table 112 is positioned so as to intersect the ring, such that a patient on the table 112 will lie over the centre of the ring 110. The table 112 is provided with a translation means 114 which is able to move the table longitudinally within the ring, i.e. from left to right in FIG. 3.

During a treatment, the linear accelerator is rotated within the ring 110 in the same way as the apparatus of FIG. 1. However, rather than rotate the table 112, it is translated within the ring in correlation with a variation in the angle θ to compensate. Thus, at all times the focal point of the radiation beam remains fixed relative to the patient. The directional approach of the radiation beam is therefore a cone rather than a plane. This can be illustrated in FIG. 4, corresponding generally to FIG. 2, in which a sphere 116 shows lines 118 illustrating the point of contact between the irradiation direction and the surface of the sphere 116. It can be seen that these described a series of concentric circles on the surface of the sphere 116, which are more akin to lines of latitude in that there is no point at which they meet. There is a gap 120 caused by the maximum value of θ, but this can be limited by suitable design in view of the physical space available for the apparatus, and is not an inherent design limitation. This therefore limits the area into which "unwanted" irradiation must be confined, and avoids any concentrated areas.

It will be understood that variations can be made to the above-described embodiment, without departing from the scope of the present invention.

What is claimed is:

1. Apparatus for treatment by radiotherapy, comprising:

a patient table, a directional radiation source directed generally toward the patient table, the table and source being movable relative to each other at least axially with respect to the table and rotationally around that axis, the source being directionally adjustable within at least a plane including the longitudinal axis of the table;

and including means to correlate axial relative motion of the table and directional adjustment of the source.

2. Apparatus according to claim 1 wherein the source can be rotated about the table to access a predetermined position along a series of cones centered on the predetermined position and of variable angle.

3. Apparatus according to claim 1, wherein the source is directionally adjustable across an included angle of at least 20°.

4. Apparatus according to claim 1, wherein the source is directionally adjustable across an included angle of at least 30°.

5. Apparatus according to claim 1, wherein the source is held within a ring member centered substantially on the patient table.

* * * * *